United States Patent [19]

Laas et al.

[11] Patent Number: 4,562,277

[45] Date of Patent: Dec. 31, 1985

[54] PROCESS FOR THE PREPARATION OF A BIS-SALICYLIDENE-ALKYLENE-DIAMINOCOBALTOUS ION COMPLEX

[75] Inventors: Harald Laas, Maxdorf; Peter Tavs, Limburgerhof; Heinz Hannebaum, Ludwigshafen; Manfred Stroezel, Ilvesheim, all of Fed. Rep. of Germany

[73] Assignee: BASF Aktiengesellschaft, Ludwigshafen, Fed. Rep. of Germany

[21] Appl. No.: 571,806

[22] Filed: Jan. 18, 1984

[30] Foreign Application Priority Data

Jan. 26, 1983 [DE] Fed. Rep. of Germany ....... 3302498

[51] Int. Cl.$^4$ ............................................. C07F 15/06
[52] U.S. Cl. ..................................................... 556/34
[58] Field of Search ........................ 260/429 C, 439 R

[56] References Cited

U.S. PATENT DOCUMENTS 2,450,276  9/1948  Fogler et al. .................... 260/429 C
3,441,578  4/1969  Dimroth .......................... 260/429 C
3,632,618  1/1972  Pancheco et al. .......... 260/429 C X
3,687,991  8/1972  Gaeng ............................. 260/429 C

OTHER PUBLICATIONS

Calderazzo, J. Chem. Soc. (A) p. 1378 (19690.

Primary Examiner—Helen M. S. Sneed
Attorney, Agent, or Firm—David L. Hedden

[57] ABSTRACT

Improved process for the preparation of salcomine useful as an oxidation catalyst for the oxidation of alkylated phenols to the corresponding alkylated p-benzoquinones by reacting salicylaldehyde with ethylenediamine in a mole ratio of about 2:1 and a cobalt salt in a liquid reaction medium wherein the reaction medium is a linear or cyclic carboxamide which is disubstituted on the nitrogen, in particular dimethylformamide, and the cobalt salt is cobalt carbonate or with the cobalt hyroxide carbonate, $2\ CoCO_3.3\ Co(OH)_2.H_2O$. Preparation of the salcomine in accordance with the invention offers significant advantages, both in the preparation of the salcomine itself and in the subsequent oxidation of the trimethylphenol to trimethyl-p-benzoquinone utilizing the salcomine.

2 Claims, No Drawings

PROCESS FOR THE PREPARATION OF A BIS-SALICYLIDENE-ALKYLENE-DIAMINOCOBALTOUS ION COMPLEX

BACKGROUND OF THE INVENTION

1. Field of the Invention

This invention relates to a process for preparation of alkylated p-benzoquinones from the corresponding alkylated phenols, in particular, trimethyl-p-benzoquinone (II) from trimethylphenol (I), by catalytic oxidation using as the catalyst a salcomine prepared by an improved process.

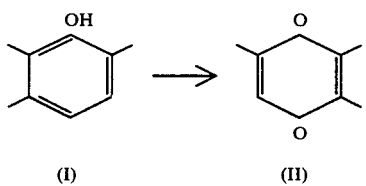

2. Description of the Prior Art

Trimethyl-p-benzoquinone (II) is a very interesting compound from a commerical standpoint, since trimethylhydroquinone, an important vitamin E precursor, can be prepared from it by means of reduction using a simple method. On a commercial level, (II) is obtained through the oxidation of trimethylphenol (I). Salcomine, a bis-salicylidene-alkylenediamino-cobaltous ion complex having the formula

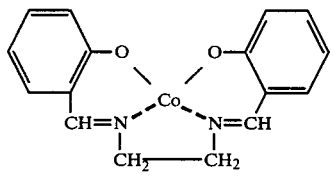

is a good catalyst for this oxidation (see DE-PS No. 17 68 063).

Numerous methods are known for the preparation of salcomine. A list of the known methods is to be found in Bull Soc. Chim. France 1976, Nos. 11–12, pp. 1717–21. In the known processes, the Schiff base derived from two moles of salicylaldehyde and one mole of ethylenediamine is reacted with a cobaltous salt either in an aqueous medium or in an aqueous organic medium. The presence of a buffer (for example, an aqueous acetic acid-sodium acetate solution or an alkanol-pyridine mixture) is recommended to better dissolve the Schiff base. The precipitating salcomine must then be filtered off, washed repeatedly, and dried. The disadvantage of this process is that the filtering, washing, and drying is very expensive on a commercial level and the resultant salcomine is not of uniform quality relative to its oxidation catalysis.

D. Aymes et al (Loc. Cit.) therefore suggests an improvement in the method of salcomine preparation wherein the salcomine is prepared in benzene, chloroform, or methylene chloride, using a cobalt compound soluble in these solutions—cobalt acetylacetonate. The disadvantages of this process are that it uses particularly expensive cobalt compounds, relies on physiologically hazardous solvents, and gives relatively poor yields of salcomine.

The invention herein is an improved process for the preparation of salcomine in which the disadvantages experienced in the prior art are no longer encountered.

SUMMARY OF THE INVENTION

The invention relates to a process for the preparation of salcomine through the reaction of salicylaldehyde with ethylenediamine in a mole ratio of about 2:1 and a cobalt salt in a liquid reaction medium wherein the salicylaldehyde is reacted with the ethylenediamine in a solvent consisting of a linear or cyclic carboxamide which is disubstituted on the nitrogen atom, preferably in dimethylformamide, and the resulting reaction mixture is further reacted at temperatures from 60° to 150° C., preferably at approximately 120° C., with a cobalt salt selected from the group consisting of cobalt carbonate and the cobalt hydroxide carbonate, 2 CoCO$_3$.3 Co(OH)$_2$.H$_2$O. The resulting salcomine is particularly useful for the oxidation of alkylated phenols to the corresponding alkylated p-benzoquinones.

DESCRIPTION OF THE PREFERRED EMBODIMENTS

The preparation of the salcomine in accordance with the invention offers considerable advantages both in the preparation of the salcomine itself and in the subsequent oxidation of the alkylated phenol, in particular of the trimethylphenol to trimethyl-p-benzoquinone.

Thus, the subject of the invention is also an improved process for the preparation of trimethyl-p-benzoquinone through the oxidation of 2,3,6- or 2,3,5-trimethylphenol with oxygen in the presence of salcomine and in the presence of a carboxamide disubstituted on the nitrogen, wherein a salcomine produced in accordance with the invention, preferably a salcomine produced in accordance with the invention in dimethylformamide is used in a dimethylformamide-moist form.

Particular advantages over the prior art which result from preparing the salcomine in accordance with the invention and from the use of the accordingly produced salcomine, are, in particular:

1. The process is simplified, since expensive washing and drying of the salcomine are no longer necessary.
2. Salcomine yields of up to 99 percent are obtained.
3. The crystallized salcomine is of uniform quality.
4. The dimethylformamide-moist salcomine is storage-stable and can be used without generating dust, which is important since inhalable dusts containing cobalt are carcinogenic.
5. The utilization of CoCO$_3$ or 2 CoCO$_3$.3 CO(OH)$_2$.H$_2$O leads to the formation of anion-free salcomine, which eliminates the adverse effects on the quality of the oxidation catalyst.
6. Utilization of salcomine prepared in accordance with the invention allows the oxidation times to be significantly shortened, whereby the quality of the trimethyl-p-benzoquinone improves and the yields are approximately 3 to 5 percent higher. Oxidation times of up to 18 hours were common with the known processes; now oxidation times of only approximately 5 to 7 hours are necessary.

It was unexpectedly found that preparing the salcomine in accordance with the invention in carboxamides which are disubstituted at the nitrogen, especially in dimethylformamide (DMF), that the reaction would run to such advantage, since earlier tests on preparing salcomine in DMF were not very successful. Calderazzo, for example, obtained a yield of only 42.5 percent when reacting octacarbonyl dicobaltate with the Schiff base of salicylaldehyde and ethylenediamine in DMF (J. Chem. Soc. (A), 1969, p. 1378 ff). This yield is not acceptable for manufacturing on a commercial level.

In the context of this invention we define carboxamides disubstituted on the nitrogen as being carboxamides of general formula III:

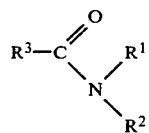

(III)

in which $R^1$, $R^2$, and $R^3$ can be the same or different, each meaning an alkyl residue having from 1 to 3 carbon atoms, and also where $R^3$ can represent a hydrogen atom or $R^2$ and $R^3$ together can represent a trimethylene group or a tetramethylene group. Typical examples are dimethylformamide, diethylformamide, or N-methylpyrrolidone. It is particularly advantageous to utilize dimethylformamide (DMF) as the solvent, since it is a relatively inexpensive solvent, and since the best salcomine yields can be produced through the use of DMF. In addition, salcomine produced in DMF yields the best results in the subsequent oxidation of the alkylated phenols.

In order to perform the process of the invention, for example, approximately a 2:1 mole ratio of salicylaldehyde to ethylenediamine is reacted in the carboxamide to form a Schiff base. During the course of this reaction the reaction mixture exotherms to from 50° to 60° C. The reaction mixture is thereupon heated to temperatures of from 60° to 150° C., preferably to approximately 120° C., and then the mixture is slowly reacted at this temperature with a molar quantity $CoCO_3$ or 0.2 moles $2 CoCO_3.3 Co(OH)_2.H_2O$ per mole of Schiff base and the resulting mixture is then stirred further for approximately 0.5 to 2 hours, preferably for approximately 1 hour. After cooling, the salcomine crystallizes out in an easily useable active form.

Generally from 2 to 4 kg solvent is used per kg salcomine.

The following cobalt compounds were tested for complexing the Schiff base from the salicylaldehyde and the ethylenediamine in DMF: $Co(OH)_2$; $CoCl_2$; $Co(NO_3)_2$; $CoSO_4$; $Co(OAc)_2$ (cobalt acetate); $CoCO_3$ and $2 CoCO_3.3 Co(OH)_2.H_2O$.

The following results were obtained. The salcomines obtained utilizing $CoCl_2$ and $Co(NO_3)_2$ do not crystallize completely. Moreover, $Co(NO_3)_2$ tends to decompose spontaneously at the reaction conditions and therefore cannot be used. When $Co(OH)_2$ was utilized, salcomine yields of only about 78 percent were obtained, which is not acceptable given the high prices for Co salts. The salcomine prepared with $CoSO_4$ catalyzed the phenol oxidation slowly, regardless of whether it was dried, while the salcomines prepared with other cobalt salts produced yields (after one hour oxidation) of approximately 90 percent in the dry state. When the reaction rates for the trimethylphenol oxidation with DMF-moist salcomines were compared, it was unexpectedly found that the rates for salcomines produced from $Co(OAc)_2$ or $Co(OH)_2$ were around 10 to 15 percent lower and only the salcomine prepared from $CoCO_3$ or from the cobalt hydroxide carbonate maintained a good yield.

The oxidation of 2,3,6-trimethylphenol or 2,3,5-trimethylphenol to form trimethyl-p-benzoquinone took place in an essentially known manner, for example, in accordance with the process described in German Pat. No. 17 93 183 or in DE-OS No. 25 18 028 so that a detailed discussion of this process using the salcomine prepared in accordance with the invention is not necessary here.

The solvents used for this oxidation are inert organic solvents which are liquid under the reaction conditions, preferably solvents belonging to the class of aprotic polar solvents, such as the linear or cyclic carboxamides, for example, dimethylformamide, diethylformamide, and N-methylpyrrolidone or aliphatic or aromatic nitriles such as acetonitrile, propionitrile, or benzonitrile.

Dimethylformamide is used as a solvent with particular advantage, since its high flash and ignition point permits safe and economic oxidation on a technical scale. The concentration of the trimethylphenol used in the reaction medium is not critical and can vary across wide ranges; preferably solutions are used containing from 5 to 30 percent by weight trimethylphenol based on the solvent.

The preferred reaction temperatures are from -10 to approximately 45° C. The reaction can be performed both at atmospheric pressure and at an elevated pressure. The oxygen partial pressures can vary within wide ranges, in particular between 0.2 and 20 bar. The oxidation and further processing of the reaction mixture are performed in the standard manner. The salcomine prepared in accordance with the invention can be added to the reaction mixture both in a dry form as well as in a carboxamide-moist form. It is particularly advantageous to utilize DMF-moist salcomine, especially when the subsequent oxidation of the alkylated phenol also is to be completed in DMF as the solvent. The improved preparation of the salcomine in accordance with the invention results in significant advantages, both in the preparation of the salcomine itself and in the subsequent oxidation of the trimethylphenol to trimethyl-p-benzoquinone in the presence of the salcomine, and therefore offers advantages for the preparation of synthetic Vitamin E.

The invention is further described in the following nonlimiting examples. All parts are given by weight unless otherwise specified.

EXAMPLE 1

(a) Two hundred forty-four parts (2 moles) salicylaldehyde were dissolved in 661 parts DMF, and this solution was reacted 30 min. with 60 parts (1 mole) ethylenediamine. The conversion to the Schiff base proceeded quantatively with heating to 60° C. The reaction mixture was then heated to 120° C. and reacted with 110 parts $CoCO_3$ (cobalt content 53 percent) for 30 minutes. This mixture was then stirred an additional hour at 120° C. with carbon dioxide being evolved and was then cooled to room temperature (RT). During the course of cooling, the salcomine precipitated in a crystalline and easily separateable form. The resulting DMF-moist salcomine could be used as an oxidation catalyst without further drying. The yield (dried salcomine relative to salicylaldehyde) was from 96 to 97 percent of theoretical.

(b) Example 1(a) was repeated, although instead of 661 parts DMF, the mother liquor accumulated in Example 1(a) was utilized after havinq had the reaction water removed from it through distillation at a reduced pressure. In this case, the resulting yields were from 98 to 99 percent of theoretical.

COMPARISON EXAMPLE I

Preparation of salcomine according to the prior art.

Sixty parts NaOH, 5 parts NaOAc, and 45 parts (0.75 mole) ethylenediamine were dissolved in 1000 parts water and 145 parts (1.5 moles) salicylaldehyde in 396 parts methanol was gradually added to this solution as the solution was stirred. The temperature increased thereby as the solution was stirred. The temperature increased to from 50° to 60° C. Then a solution of 178.5 parts $CoCl_2.6H_2O$ in 750 parts water was added to this reaction mixture in 60 min. at 60° C. After the addition had been completed, the mixture was stirred for an additional 5 to 10 min. then suction filtered off hot, and the precipitate was washed with 2000 parts water. Then the precipitated salcomine was again slurried in 4000 parts water and stirred for 20 min. at 60° C. After suction filtration the salcomine was dried at 100° C. and at a pressure reduced to 12 mbar. The dried salcomine yield was 197.4 parts corresponding to 81 percent of theoretical.

EXAMPLES AND COMPARISON EXAMPLES FOR THE OXIDATION OF 2,3,6-TRIMETHYLPHENOL (TMP) TO TRIMETHYL-P-BENZOQUINONE (TMQ)

Various salcomines were prepared by reacting salicylaldehyde with an equivalent amount of ethylenediamine in dimethylformamide, and the resulting reaction mixture was reacted with the equivalent amount of the cobalt salts listed in the following table at approximately 120° C. The weighing of the salcomine was based on the cobalt content. The DMF-moist salcomines were then recalculated to dry product.

Then, 70 parts 2,3,6-trimethylphenol (TMP) in 205 parts DMF was oxidized with oxygen in the presence of the salcomines listed in the table below and with rapid stirring. During the oxidation reaction the temperature was maintained at from 40° to 45° C.

After a reaction time of 1 hour, the reaction was interrupted and the conversion of TMP to trimethyl-p-benzoquinone (TMQ) was determined by means of gas chromatography (GC).

The TMQ yield after 1 hour obtained with DMF-moist salcomine and dried salcomine is shown in the table.

TABLE

| Salcomine Prepared by utilizing | TMQ Yield after 1 h [% of Theoretical] | |
|---|---|---|
| | DMF-Moist Salcomine | Obtained with Dried Salcomine |
| Example | | |
| 2 | $CoCO_3$ | 91.5 | 91.5 |
| 3 | 2 $CoCO_3.3$ $Co(OH)_2.H_2O$ | 90.5 | 91.5 |
| Comparison Example | | |
| I | $CoCl_2.6 H_2O$ | — | 70 |

TABLE-continued

| Salcomine Prepared by utilizing | TMQ Yield after 1 h [% of Theoretical] | |
|---|---|---|
| | DMF-Moist Salcomine | Obtained with Dried Salcomine |
| II | $CoSO_4$ | 25 | 33 |
| III | $Co(OAc)_2$ | 77 | 88 |
| IV | $Co(OH)_2$ | 79 | 91 |

EXAMPLE 4

Demonstration of the stability of DMF-moist salcomine

The tests described above with salcomine prepared utilizing $CoCO_3$ or 2 $CoCo_3.3$ $Co(OH)_2.H_2O$ was repeated after the DMF-moist salcomines had been stored for 5 months. No differences were established relative to the tests described above.

EXAMPLE 5

(a) Preparation of Salcomine in N-Methyl-pyrrolidone

Thirty parts ethylenediamine was added dropwise to a stirred solution of 350 parts N-methylpyrrolidone and 122 parts salicylaldehyde in 30 min. The temperature of the reaction mixture increased during this addition to 60° C. The mixture was then heated to 120° C. and 62.7 parts 2 $CoCO_3.3$ $Co(OH)_2.H_2O$ (cobalt content 47 percent) was added by portions. After the $CO_2$ generation had stopped, (approximately 30 min), stirring was continued for an additional hour at 120° C., then the mixture was cooled to RT, the crystalline salcomine was filtered off by suction and dried at a reduced pressure. The yield was 145.3 parts salcomine corresponding to 89.4 percent of theoretical.

(b) Oxidation of TMP to TMQ

The salcomine obtained in Example 4(a) was utilized as described above for the oxidation of TMP to TMQ. After 1 hour oxidation time the conversion of TMP to TMQ was 80.5 percent.

EXAMPLE 6

(a) Preparation of Salcomine in N,N-Diethylformamide

The salcomine was prepared as described in Example 4, however, 350 parts N,N-diethylformamide was used as the solvent in place of 350 parts N-methylpyrrolidone. The yield was 147.9 parts salcomine, corresponding to 91.2 percent of theoretical.

(b) Oxidation of TMP to TMQ

The salcomine obtained in accordance with Example 5(a) was utilized as described above for the oxidation of TMP to TMQ. After 1 hour oxidation time the conversion of TMP to TMQ was 82.7 percent.

The embodiments of the invention in which an exclusive privilege or property is claimed are defined as follows:

1. An improved process for the preparation of a bis-salicylidene-alkylenediamino-cobaltous ion complex by reacting salicylaldehyde with ethylenediamine in a mole ratio of about 2:1 and a cobalt salt wherein the salicylaldehyde and ethylenediamine are reacted in a solvent consisting of a linear or cyclic carboxamide which is disubstituted on the nitrogen atom and wherein the resultant reaction mixture is further reacted with a cobalt salt selected from the group consisting of cobalt carbonate and cobalt hydroxide carbonate at temperatures of 60° C. to 150° C.

2. The process of claim 1 wherein the solvent is dimethylformamide.

* * * * *